United States Patent
Vaughn et al.

[11] Patent Number: 5,952,538
[45] Date of Patent: Sep. 14, 1999

[54] USE OF SHORT CONTACT TIME IN OXYGENATE CONVERSION

[75] Inventors: Stephen Neil Vaughn; David R. Lumgair, both of Kingwood; Hsiang-ning N. Sun, Houston, all of Tex.

[73] Assignee: Exxon Chemical Patents Inc., Houston, Tex.

[21] Appl. No.: 08/880,962

[22] Filed: Jun. 23, 1997

Related U.S. Application Data

[60] Provisional application No. 60/034,115, Dec. 31, 1996, abandoned.

[51] Int. Cl.[6] .................................................. C07C 1/00
[52] U.S. Cl. ........................ 585/640; 585/638; 585/639
[58] Field of Search .................... 585/638, 639, 585/640; 502/214, 240

[56] References Cited

U.S. PATENT DOCUMENTS

| | | | |
|---|---|---|---|
| 4,052,479 | 10/1977 | Chang et al. | 260/682 |
| 4,069,136 | 1/1978 | Peer et al. | 208/65 |
| 4,440,871 | 4/1984 | Lok et al. | 502/214 |
| 4,499,327 | 2/1985 | Kaiser | 585/460 |
| 4,677,243 | 6/1987 | Kaiser | 585/638 |
| 5,095,163 | 3/1992 | Barger | 585/640 |
| 5,126,308 | 6/1992 | Barger et al. | 502/214 |
| 5,157,181 | 10/1992 | Stine et al. | 585/329 |

FOREIGN PATENT DOCUMENTS

| | | |
|---|---|---|
| 0 485 145 | 5/1992 | European Pat. Off. |
| 2 093 721 | 9/1982 | United Kingdom . |
| WO 93/24430 | 12/1993 | WIPO . |
| WO 93/24431 | 12/1993 | WIPO . |

OTHER PUBLICATIONS

"Free Fall Reactor" *Fluidization Engineering*, D. Kunii and O. Levenspiel, Robert E. Krieger Publishing Co. NY, 1977.
"Riser Reactor" *Fluidization and Fluid–Particle Systems*, pp. 48–59, F. A. Zenz and D. F. Othmo, Reinhold Publishing Corp., NY 1960.

*Primary Examiner*—Glenn Caldarola
*Assistant Examiner*—In Suk Bullock
*Attorney, Agent, or Firm*—Bradley A. Keller

[57] ABSTRACT

The present invention relates to methods for the converting oxygenates to olefins. More particularly, the invention relates to methods for converting oxygenates to olefins with improved olefin yields and decreased yields of undesirable methane and other light saturate byproducts.

18 Claims, No Drawings

USE OF SHORT CONTACT TIME IN OXYGENATE CONVERSION

The present application claims priority from now abandoned U.S. Provisional Patent Application Ser. No. 60/034,115 which was entitled "USE OF SHORT CONTACT TIME IN OXYGENATE CONVERSION" and which was filed Dec. 31, 1996. The applicants hereby incorporate that application by reference in its entirety.

FIELD OF THE INVENTION

The present invention relates to methods for converting oxygenates to olefins. More particularly, the invention relates to methods for converting oxygenates to olefins with improved olefin yields and decreased yields of methane and other light saturate byproducts.

BACKGROUND OF THE INVENTION

Olefins have been traditionally produced from petroleum feedstocks by either catalytic or steam cracking. Unfortunately, the cost of petroleum cracking has steadily increased, making it important to find alternative feedstock sources for olefins.

Oxygenates, such as alcohols, are a promising alternative feedstock for making olefins. Alcohols may be derived from nonpetroleum sources, such as sugar. The fermentation of sugar produces ethanol. Alcohols also can be produced from synthesis gas. Synthesis gas can be produced from a number of organic materials, including but not limited to recycled plastics, municipal wastes, petroleum liquids, natural gas, carbonaceous materials including coal, and other organic material.

The prior art in the area of olefin generation from oxygenates, such as methanol and di-methyl ether, focuses on maximizing ethylene and propylene product yields as exemplified in U.S. Pat. Nos. 4,499,327, 4,677,243, 5,095,163, and 5,126,308. The total yield slate, typically includes light saturates with a molecular weight lower than ethylene, i.e. methane ($CH_4$), hydrogen ($H_2$), carbon monoxide (CO), carbon dioxide ($CO_2$), and ethane ($C_2^O$), and heavier by-products with a molecular weight higher than propylene, i.e. C4's and C5's. In the prior art, little attention has been given to the overall optimization of the yield slate other than to minimize the C4's and heavier due to the fouling potential and relatively lower value of these by-products.

The production of the light saturates by-products has not been a problem to be addressed since these byproducts are "clean" compounds without any fouling potential and can be readily recovered for at least fuel value. Therefore, the prevailing focus in the prior art has been not to address minimizing the light saturates yields.

The disadvantage of this approach is that one must include costly separation facilities in the olefin production plant to first separate and then recover the methane and other light saturates from the desired ethylene and propylene products. Such recovery schemes typically include a cold box, a demethanizer, a deethanizer, and a ethylene/ethane splitter. Even though the various separations techniques are well known in the art, this equipment must generally operate at temperatures of −200° C. (−328° F.) and below, which require materials constructed of very expensive stainless steel alloys, as carbon steel piping becomes brittle and breaks when operating at temperatures below −100° C. Heretofore, the prior art has not taught an effective way to minimize the methane and other light saturates yields to minimize the investment in such recovery facilities.

The production of methane from oxygenate feeds for a given catalyst can be reduced by lowering the reaction temperature. However, lowering the temperature also reduces catalyst activity and ethylene yield. The industry needs a method to produce olefins at high temperatures from oxygenates which achieves higher olefin yields with reduced light saturate yields.

SUMMARY OF INVENTION

The present invention provides a method for converting an oxygenate feed to olefins comprising contacting an oxygenate feed with a molecular sieve catalyst under effective conditions to convert the oxygenate feed to olefins and byproducts including methane, wherein said conditions comprise a weight hourly space velocity (WHSV) of at least about 20 $hr^{-1}$ to produce a Temperature Corrected Normalized Methane Selectivity (TCNMS) of less than about 0.016.

DETAILED DESCRIPTION OF THE INVENTION

The following parameters, used in defining the invention, are helpful to evaluate the effectiveness of the present invention in reducing the methane yield relative to the yield of a desired product—typically ethylene. "Methane selectivity" is the yield of methane produced upon conversion of the oxygenate feedstock, on either a weight or molar basis, divided by the degree of conversion of the oxygenate feedstock measured on the same basis. The term "Normalized Methane Selectivity" or "NMS" is defined as the methane product yield divided by the ethylene product yield wherein each yield is measured on or is converted to a weight % basis. The term "Temperature Corrected Normalized Methane Selectivity" or "TCNMS" is defined as the NMS when the temperature is less than 400° C. When the temperature is 400° C. or greater, the TCNMS is defined by the following equation, in which T=temperature in ° C.:

$$TCNMS = \frac{NMS}{(1 + ((T - 400)/400) \times 14.84)}$$

The lower the NMS and/or TCNMS, the more effective the process is in maximizing ethylene yield and minimizing methane yield.

The present invention provides a method for optimizing the yield slate during the conversion of oxygenates, where the reaction conditions comprise a weight hourly space velocity (WHSV) of at least about 20 $hr^{-1}$ producing olefins having a TCNMS of less than about 0016. In a preferred process, the olefins are produced at temperature of at least 300° C. In another preferred process, the olefins are produced at temperatures of about 400° C. or higher and have TCNMS of less than about 0.01. Owing to the nature of the process, it may be desirable to carry out the process of the present invention by use of the molecular sieve catalysts in a dynamic bed system or any system of a variety of transport beds rather than in a fixed bed system. The critical feature of the reactor system utilized is the ability to operate at high space velocities.

The conversion of oxygenates to produce light olefins may be carried out in a variety of catalytic reactors, including, but not limited to, fluid bed reactors and concurrent riser reactors as described in "Free Fall Reactor," *Fluidization Engineering*, D. Kunii and O. Levenspiel, Robert E. Krieger Publishing Co. NY, 1977, incorporated in its entirety by reference herein. Additionally, countercurrent free fall reactors may be used in the conversion process as described in U.S. Pat. No. 4,069,136 and "Riser Reactor", *Fluidization and Fluid-Particle Systems*, pages 48–59, F. A. Zenz and D. F. Othmo, Reinhold Publishing Corp., NY 1960 are also incorporated in their entirety by reference herein. It is well understood by those skilled in the art that each type of reactor will have advantages and disadvantages in any particular application.

In a preferred process, th olefins are produced at temperatures of about 400° C. or higher and have a TCNMS of less than about 0.01. Preferred reactors are co-current riser reactors and short contact time countercurrent free-fall reactors in which an oxygenate feedstock can be contacted with a molecular sieve catalyst at a weight hourly space velocity (WHSV) of at least about 20 $hr^{-1}$, preferably in the range of from about 20 $hr^{-1}$ to 1000 $hr^{-1}$, and most preferably in the range of from about 20 $hr^{-1}$ to 500 $hr^{-1}$. Because the catalyst or the feedstock may contain other materials which act as inerts or diluents, the WHSV is calculated on the weight basis of the oxygenate feed and the molecular sieve used.

The molecular sieve catalyst may be a large, medium, or small pore catalyst. Typically, large pore catalysts are defined as having a pore size of more than about 10 Angstrom units, while medium pore catalysts are defined as having a pore size of less than 10 and greater than 5 Angstrom units. A preferred embodiment uses a small pore molecular sieve catalyst having a pore size ranging from about 3.5 to about 5.0 Angstroms units, preferably from about 4.0 to about 5.0 Angstroms, and most preferably from about 4.3 to about 5.0 Angstroms. Suitable molecular sieve catalysts include, but are not necessarily limited to, silicoaluminophospate (SAPO) catalysts, Mordenite zeolite, ZSM-5, ZSM-34, chabazite, erionite, and mixtures thereof, preferably a SAPO catalyst, SAPO-5, SAPO-11, SAPO-34, SAPO-17, SAPO-18, SAPO44, and most preferred SAPO-17, SAPO-18, SAPO-34, SAPO44, ZSM-34, chabazite, and erionite. A metal may be incorporated into the selected catalyst, using either in-situ or post synthesis methods well known to those skilled in the catalyst synthesis art.

The starting material (feedstock) comprises "oxygenates" which are defined for purposes of this invention to comprise organic molecules containing oxygen atoms, such as aliphatic alcohols, ethers, carbonyl compounds (aldehydes, ketones, carboxylic acids, carbonates, and the like), and organic molecules containing atoms, such as halides, mercaptans, sulfides, amines, and mixtures thereof. The aliphatic moiety preferably contains from 1 to 10 carbon atoms and more preferably contains from 1 to 4 carbon atoms. Representative oxygenates include but are not necessarily limited to lower straight and branched chain aliphatic alcohols, their unsaturated counterparts and the nitrogen, halogen and sulfur analogues of such. Examples of suitable compounds include, but are not limited to: methanol; ethanol; n-propanol; isopropanol; $C_4$–$C_{20}$ alcohols; methyl ethyl ether; dimethyl ether; diethyl ether; di-isopropyl ether; methyl mercaptan; methyl sulfide; methyl amine; ethyl mercaptan; diethyl sulfide; diethyl amine; ethyl chloride; formaldehyde; dimethyl carbonate; dimethyl ketone; acetic acid; n-alkyl amines, n-alkyl halides, n-alkyl sulfides, each having n-alkyl groups comprising between about 3 to 10 carbon atoms; and mixtures thereof. The term "oxygenate" as employed herein designates only the organic material used as the feed. The total charge of feed to the reaction zone may contain additional compounds such as diluents. Optionally, any unconverted feed may be recovered and recycled to the conversion reactor along with fresh feed.

The conversion may be carried out in the vapor phase at process conditions so as to produce the desired olefins, i.e., an effective temperature, pressure, WHSV (Weight Hourly Space Velocity) and, optionally, an effective amount of diluent, correlated to produce olefins. Alternately, the process may be carried out in the liquid phase, which may result in different rates of conversion and selectivity of feedstock-to-product with respect to the relative ratios of the light olefin products.

The reaction temperature may vary over a wide range depending, at least in part, on the selected molecular sieve catalyst. An effective temperature may be in, but is not necessarily limited to, the range of from about 200° C. to about 700° C., preferably of from about 250° C. to about 600° C., and most preferably of from about 300° C. to about 500° C. At the lower end of the temperature range, the formation of the desired light olefin product(s) may become markedly slow. At the upper end of the reactioned temperature range and beyond, the process may not form an optimum amount of light olefin products. In a preferred embodiment, which results in a particularly desirable low TCNMS, the temperature is at least about 400° C.

The pressure also may vary over a wide range, including autogeneous pressures. Effective pressures may be in, but are not necessarily limited to, pressures of from about 0.1 kPa to about 100 MPa. Preferred pressures are in the range of about 6.9 kPa to about 34 MPa, with the most preferred range being of from about 48 kPa to about 0.34 MPa. The foregoing pressures are exclusive of any inert diluent, and thus, refer to the partial pressure of the oxygenate compounds and/or mixtures thereof with feedstock. At the lower and upper end of the foregoing pressure ranges, the rate of selectivity, conversion and/or reaction may not be optimum.

The residence time may vary from seconds to a number of hours, determined largely by the reaction temperature, the pressure, the molecular sieve catalyst selected, the WHSV, the phase (liquid or vapor), and the process design characteristics.

One or more inert diluents may be present in the feedstock, for example, in an amount of from 1 to 99 molar percent, based on the total number of moles of all feed and diluent components fed to the reaction zone (or catalyst). Typical diluents include, but are not necessarily limited to helium, argon, nitrogen, carbon monoxide, carbon dioxide, hydrogen, water, paraffins, hydrocarbons (such as methane), aromatic compounds, and mixtures thereof. The preferred diluents are water and nitrogen.

The process may be carried out in a batch, semi-continuous or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of the molecular sieves in series to provide for a desired product mixture.

If regeneration is required, the molecular sieve catalyst can be continuously introduced as a moving bed to a regeneration zone where it can be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The invention will be better understood with reference to the following examples.

EXAMPLE I

Comparative

The following is an analysis of the methane selectivity resulting from a typical methanol to olefin process as represented in the prior art, and which is not the subject of the present invention. Like most methanol to olefin processes, the process described in U.S. Pat. No. 4,499,327 is designed to maximize ethylene and propylene yields. U.S. Pat. No. 4,499,327 specifies a WHSV in the range of from about 0.01 hr$^{-1}$ to about 100 hr$^{-1}$, preferably in the range of from about 0.1 hr$^{-1}$ to about 40 hr$^{-1}$. U.S. Pat. No. 4,499,327 also teaches that WHSV above 100 hr$^{-1}$ may be employed, though such values are not preferred (column 7, lines 28–34). The process is said to result in a methane selectivity of less than 10 molar %, with 5 molar % being preferred (column 6, lines 13–21). These selectivity numbers as measured on a molar basis are equivalent on a weight basis to 5 wt. % and 2.5 wt. %, respectively.

Example 32 of U.S. Pat. No. 4,499,327 uses SAPO-34 as a catalyst for the conversion of methanol to light olefins at a WHSV of approximately 0.8 hr$^{-1}$ under the autogeneous pressure and at four different temperatures: 350° C., 375° C., 400° C., and 425° C. The results are reproduced and reported in units of mole % and wt % in Table I below.

TABLE I

| Reaction Temperature | 350° C. | 375° C. | 400° C. | 425° C. |
|---|---|---|---|---|
| Methane Selectivity, wt. % (mol %) | 0.7 (1.7) | 0.6 (1.3) | 0.9 (2.0) | 2.0 (4.1) |
| Ethylene Selectivity, wt. % (mol %) | 26.4 (37.0) | 32.5 (42.6) | 35.7 (46.0) | 41.2 (48.6) |
| NMS | 0.0263 | 0.0174 | 0.0248 | 0.0482 |
| TCNMS | 0.0263 | 0.0174 | 0.0278 | 0.0248 |

While a methane selectivity of less than 2.5 wt. % (5 mol %) is achieved, one can see that both the ethylene and methane selectivity increase with increasing temperature; however, the methane yield increases at a much faster rate than the ethylene yield.

With respect to the effect of WHSV and its impact on the yield slate, U.S. Pat. No. 4,499,327 does not specify any narrow range of WHSV's that produce any better or worse results. In fact, Example 34 of U.S. Pat. No. 4,499,327 teaches that flow rate, as characterized by WHSV, does not substantially affect the methane production. Two sets of examples are presented to illustrate the effect of flow rate on light olefin production, with the second flow rate being approximately 2.5 times greater than the first flow rate. The results are reproduced and reported in units of mole % and weight % in Table II below.

Comparison of the data presented in Table II, after substantially the same time on stream, shows that the ethylene selectivity is generally lower at the higher WHSV (1.91 hr$^{-1}$) than at the lower WHSV (0.83 hr$^{-1}$) and the methane selectivity is sometimes higher and sometimes lower. The net result of this variability is that the NMS also is sometimes higher and sometimes lower at the two different WHSV's. Thus, no clear advantage is seen from the use of a higher WHSV.

EXAMPLE II

Comparative

SAPO-34 was prepared as described in U.S. Pat. No. 4,440,871, incorporated herein by reference. 5.0 cc of the prepared SAPO-34 catalyst was mixed with 15 cc of quartz beads and loaded into a 1.9 cm (¾") outer diameter 316 stainless steel tubular reactor which was heated by a three-zone electric furnace. The first zone, acting as the preheating zone, vaporized the feed. The temperature of the center zone of the furnace was adjusted to give the desired reaction temperature of 450° C. The reactor was purged first with nitrogen at 50 cc/min. flow rate for 30 minutes. The feed, containing 30.8 wt. % methanol, equivalent to a 4:1 (molar ratio) of water and methanol, was pumped into the reactor and calibrated to give a flow rate of 0.7 hr$^{-1}$ WHSV at a pressure of (3 psig). The results are tabulated as follows:

| WHSV, hr$^{-1}$ | T, °C. | CH$_4$, wt % | C$_2$H$_4$, wt % | NMS | TCNMS | Conversion % |
|---|---|---|---|---|---|---|
| 0.7 | 450 | 2.90 | 50.80 | 0.0571 | 0.0200 | 100.0 |

The methanol conversion was 100%. The effluent was analyzed at pre-determined intervals by an on-line gas chromatograph fitted with both a thermal conductivity detector and a flame ionization detector. The process resulted in a NMS of approximately 0.06 and a TCNMS of 0.02.

EXAMPLE III

Invention

A sample of SAPO-34 was prepared by calcining the catalyst powder at 650° C. for 2 hours in air. 50.5 mg of the

TABLE II

| Example 34 WHSV, hr$^{-1}$ | Set 1 0.83 | | | | Set 2 1.91 | |
|---|---|---|---|---|---|---|
| Methane Selectivity, wt. % (mol %) | 0.57 (1.4) | 0.61 (1.4) | 0.58 (1.3) | 0.73 (1.5) | 0.49 (1.2) | 0.39 (0.9) |
| Ethylene Selectivity, wt. % (mol %) | 27.2 (38.2) | 30.1 (39.4) | 33.1 (42.6) | 31.7 (37.3) | 27.5 (38.6) | 21.9 (28.7) |
| NMS | 0.021 | 0.020 | 0.017 | 0.023 | 0.018 | 0.018 |
| TCNMS | 0.021 | 0.020 | 0.017 | 0.023 | 0.018 | 0.018 |
| Conversion | 100% | 100% | 100% | 100% | 100% | 72.5% |
| Hours on Stream | 0.9 | 1.7 | 5.2 | 0.8 | 1.5 | 3.8 |
| Temperature, °C. | | | 375° C. | | | | prepared catalyst was added to a 4 mm internal diameter quartz reactor fitted with glass wool above and below the catalyst charge. The reactor was heated to 450° C. Total pressure was held at 5 psig. Samples of 1 microliter of a water/methanol blend (4:1 molar ratio) were repeatedly injected over the catalyst at a WHSV of 21 hr$^{-1}$. The water and methanol were heated to the reactor temperature upon injection into the reactor. The products and unreacted feed were measured using a gas chromatograph equipped with a flame ionization detector, giving the following results:

| WHSV, hr$^{-1}$ | T, °C. | CH$_4$, wt % | C$_2$H$_4$, wt % | NMS | TCNMS | Conversion % |
|---|---|---|---|---|---|---|
| 21 | 450 | 1.56 | 38.90 | 0.0401 | 0.01400 | 100.0 |

The resulting NMS was 0.040 and the TCNMS was 0.014. From the foregoing, it was concluded that increasing the WHSV from 0.7 hr$^{-1}$ to 21 hr$^{-1}$ decreased the NMS and the TCNMS each by about 30%.

EXAMPLE IV

Invention

The procedures of Example III were repeated except that only 50.0 mg of the catalyst and no diluent were used and the reaction pressure was increased to 25 psig. The WHSV was increased from 21 hr$^{-1}$ to 110 hr$^{-1}$, and five different temperatures were used: 325° C., 375° C., 425° C., 450° C., and 475° C. The following results were achieved:

| WHSV, hr$^{-1}$ | T, °C. | CH$_4$, wt % | C$_2$H$_4$, wt % | NMS | TCNMS | Conversion % |
|---|---|---|---|---|---|---|
| 110 | 325 | 0.37 | 26.92 | 0.0137 | 0.01370 | 42.0 |
|  | 375 | 0.42 | 29.26 | 0.0144 | 0.01440 | 73.2 |
|  | 425 | 0.54 | 33.11 | 0.0163 | 0.00846 | 96.7 |
|  | 450 | 0.61 | 32.72 | 0.0186 | 0.00653 | 99.2 |
|  | 475 | 0.95 | 39.85 | 0.0238 | 0.00630 | 100.0 |

At temperature 450° C. and with a WHSV of 110 hr$^{-1}$, the NMS was reduced from 0.0401 (Example III, at the same temperature of 450° C. and with a WHSV of 21 hr$^{-1}$) to 0.0186. The corresponding TCNMS was reduced from 0.0140 to 0.00653.

EXAMPLE V

Invention

The procedures of Example IV were repeated except that a smaller charge of catalyst, 21.1 mg, was used and the WHSV was increased to from 110 hr$^{-1}$ to 215 hr$^{-1}$, giving the following results at the following temperatures:

| WHSV, hr$^{-1}$ | T, °C. | CH$_4$, wt % | C$_2$H$_4$, wt % | NMS | TCNMS | Conversion % |
|---|---|---|---|---|---|---|
| 215 | 325 | 0.32 | 28.48 | 0.0112 | 0.01120 | 17.6 |
|  | 375 | 0.41 | 28.98 | 0.0141 | 0.01410 | 42.5 |
|  | 425 | 0.52 | 32.69 | 0.0160 | 0.00830 | 77.2 |
|  | 450 | 0.64 | 33.00 | 0.0194 | 0.00680 | 94.7 |
|  | 475 | 0.95 | 39.36 | 0.0241 | 0.00637 | 95.1 |

At temperature of 450° C. and with a WHSV of 215 hr$^{-1}$, the NMS was 0.0236 and the calculated TCNMS was 0.0068.

EXAMPLE VI

Invention

The procedures of Example IV were repeated except that 5.5 mg of catalyst was used and the WHSV was increased to approximately 430 hr$^{-1}$, giving the following results at various reading temperatures:

| WHSV, hr$^{-1}$ | T, °C. | CH$_4$, wt % | C$_2$H$_4$, wt % | NMS | TCNMS | Conversion % |
|---|---|---|---|---|---|---|
| 430 | 325 | 0.19 | 27.98 | 0.0068 | 0.00680 | 16.4 |
|  | 375 | 0.32 | 30.37 | 0.0105 | 0.01050 | 42.2 |
|  | 425 | 0.44 | 33.63 | 0.0131 | 0.00680 | 69.6 |
|  | 450 | 0.51 | 33.03 | 0.0154 | 0.00539 | 85.7 |
|  | 475 | 0.73 | 40.27 | 0.0181 | 0.00479 | 87.3 |

Thus, at a temperature of 450° C. and with a WHSV of 430 hr$^{-1}$, the NMS was 0.0154 and the TCNMS was 0.00539. At 475° C., the TCNMS was even lower, at 0.00479.

EXAMPLE VII

Invention

The procedures of Example IV were repeated except that 5.5 mg of catalyst was used, and the WHSV was increased to approximately 1000 hr$^{-1}$, giving the following results:

| WHSV, hr$^{-1}$ | T, °C. | CH$_4$, wt % | C$_2$H$_4$, wt % | NMS | TCNMS | Conversion % |
|---|---|---|---|---|---|---|
| 1000 | 450 | 0.54 | 40.34 | 0.0134 | 0.00469 | 31.3 |

At the temperature of 450° C. and with the WHSV of 1000 hr$^{-1}$, the NMS was 0.0134 and the resulting TCNMS was 0.00469.

The examples illustrate how it is achievable and advantageous through the use of the present invention, to produce higher yields of olefins from oxygenates at high temperatures with reduced methane and other light saturate yields; thus, overcoming the problems in the prior art wherein lower temperatures, which resulted in undesirable lower olefin yields, were required in order to be able to reduce light saturate yields.

Persons of ordinary skill in the art will recognize that many modifications may be made to the present invention without departing from the spirit and scope of the present invention. The embodiments described herein are meant to be illustrative only and should not be taken as limiting the invention, which is defined in the following claims.

We claim:

1. A method for converting an oxygenate feed to olefins comprising the step of contacting an oxygenate feed with a silicoaluminophosphate (SAPO) molecular sieve catalyst under conditions effective to convert said oxygenate feed to olefins and byproducts including methane, wherein said conditions comprise a weight hourly space velocity (WHSV) of at least about 20 hr$^{-1}$ and a Temperature Corrected Methane Selectivity (TCNMS) of less than about 0.016.

2. The method of claim 1 wherein said conditions comprise a temperature of at least about 300° C.

3. The method of claim 2 wherein said conditions comprise a temperature of in the range of from about 300° C. to about 500° C.

4. The method of claim 3 wherein said conditions comprise a temperature of in the range of from about 400° C. to about 500° C.

5. The method of claim 3 wherein said conditions comprise a WHSV in the range of from about 20 hr$^{-1}$ to about 500 hr$^{-1}$.

6. The method of claim 1 wherein said conditions comprise a weight hourly space velocity (WHSV) in the range of from about 20 hr$^{-1}$ to about 1000 hr$^{-1}$ and a temperature of in the range of from about 300° C. to about 500° C.

7. The method of claim 1 wherein said silicoaluminophosphate molecular sieve catalyst is selected from the group consisting of SAPO-17, SAPO-18, SAPO-34, and SAPO-44.

8. The method of claim 7 wherein said molecular sieve catalyst is SAPO-34.

9. The method of claim 7 wherein said silicoaluminophosphate molecular sieve catalyst has a pore size greater than 3.5 Angstroms and less than about 5.0 Angstroms.

10. The method of claim 9 wherein said silicoaluminophosphate molecular sieve catalyst has a pore size greater than 4.0 Angstroms and less than about 5.0 Angstroms.

11. The method of claim 10 wherein said silicoaluminophosphate molecular sieve catalyst has a pore size greater than 4.3 Angstroms and less than about 5.0 Angstroms.

12. The method of claim 1 wherein said passing of said oxygenate feed over said molecular sieve catalyst is accomplished in a reactor selected from the group consisting of a free fall reactor, a fluidized bed reactor, and a riser reactor.

13. The method of claim 1 wherein said oxygenate feed is selected from the group consisting of organic molecules containing oxygen atoms, aliphatic alcohols, ethers, carbonyl compounds, organic molecules containing halides, mercaptans, sulfides, amines, and mixtures thereof.

14. The method of claim 13 wherein said oxygenate feed is selected from the group consisting of organic molecules with an aliphatic moiety of 1 to 10 carbon atoms.

15. The method of claim 14 wherein said oxygenate feed is selected from the group consisting of organic molecules with an aliphatic moiety of 1 to 4 carbon atoms.

16. The method of claim 1 wherein said Temperature Corrected Normalized Methane Selectivity (TCNMS) is less than or equal to about 0.01.

17. A method for converting an oxygenate feed to olefins comprising the step of contacting an oxygenate feed with a silicoaluminophosphate molecular sieve catalyst under effective conditions to convert said oxygenate feed to olefins and byproducts including methane, wherein said oxygenate feed is selected from the group consisting of organic molecules containing oxygen atoms, aliphatic alcohols, ethers, carbonyl compounds, organic molecules containing halides, mercaptans, sulfides, amines, and mixtures thereof, wherein said molecular sieve catalyst has a pore size greater than 3.5 Angstroms and less than about 5.0 Angstroms, and wherein said conditions comprise a weight hourly space velocity (WHSV) from about 20 hr$^{-1}$ to about 500 hr$^{-1}$; a temperature from about 300° C. to about 500° C.; and a Temperature Corrected Normalized Methane Selectivity (TCNMS) of less than about 0.016.

18. A method for converting an oxygenate feed including methanol to olefins to minimize light saturate yields, said method comprising the step of contacting an oxygenate feed including methanol with a SAPO-34 molecular sieve catalyst under effective conditions to convert said oxygenate feed to olefins and byproducts including methane, wherein said oxygenate feed is selected from the group consisting of organic molecules with an aliphatic moiety of 1 to 4 carbon atoms and includes, at least, methanol, wherein said contacting of said oxygenate feed with said SAPO-34 molecular sieve catalyst is accomplishing by passing said oxygenate feed over said SAPO-34 molecular sieve catalyst and said SAPO-34 molecular sieve catalyst is not in a stationary position, and wherein said conditions comprise a weight hourly space velocity (WHSV) of from 20 hr$^{-1}$ to about 500 hr$^{-1}$; a temperature from about 400° C. to about 500° C.; and a Temperature Corrected Normalized Methane Selectivity (TCNMS) of less than about 0.01.

* * * * *